United States Patent [19]

Muller et al.

[11] 4,287,304

[45] Sep. 1, 1981

[54] FERMENTABLE SUGAR FROM THE HYDROLYSIS OF STARCH DERIVED FROM DRY MILLED CORN

[75] Inventors: Werner C. Muller, Dobbs Ferry, N.Y.; Franklyn D. Miller, Cincinnati, Ohio

[73] Assignee: National Distillers and Chemical Corp., New York, N.Y.

[21] Appl. No.: 112,033

[22] Filed: Jan. 14, 1980

[51] Int. Cl.³ .............................................. C12P 7/14
[52] U.S. Cl. ...................................... 435/162; 435/99; 435/161; 426/11; 426/48; 127/38; 127/69
[58] Field of Search ...................... 435/99, 96; 127/38, 127/68, 69, 70; 426/11, 48

[56] References Cited

U.S. PATENT DOCUMENTS

| | | | |
|---|---|---|---|
| 2,698,826 | 1/1955 | Peltzer, Sr. | 435/161 |
| 3,236,740 | 2/1966 | Smith et al. | 435/161 |
| 3,251,717 | 5/1966 | Honeychurch et al. | 127/69 X |
| 4,069,103 | 1/1978 | Muller | 435/99 |
| 4,089,745 | 5/1978 | Antrim et al. | 435/99 |
| 4,181,748 | 1/1980 | Chwalek et al. | 127/68 X |
| 4,217,414 | 8/1980 | Walon | 435/99 X |

Primary Examiner—Lionel M. Shapiro
Attorney, Agent, or Firm—Kenneth D. Tremain

[57] ABSTRACT

Starch derived from dry milled corn is hydrolyzed to provide a sterile aqueous fermentable sugar solution which is especially adapted for fermentative conversion to ethanol with minimum thermal expenditure. Following an initial mild hydrolysis to thin, or liquefy, the starch, substantially all of the water insoluble protein and oil components, and a portion of the water soluble components, e.g., sugars, lipids, proteins and vitamins, are separately recovered from the partial starch hydrolysate with the water solubles being recycled to the system. Thereafter, the partial starch hydrolysate is subjected to further hydrolysis to provide an aqueous solution of fermentable sugar.

13 Claims, 1 Drawing Figure

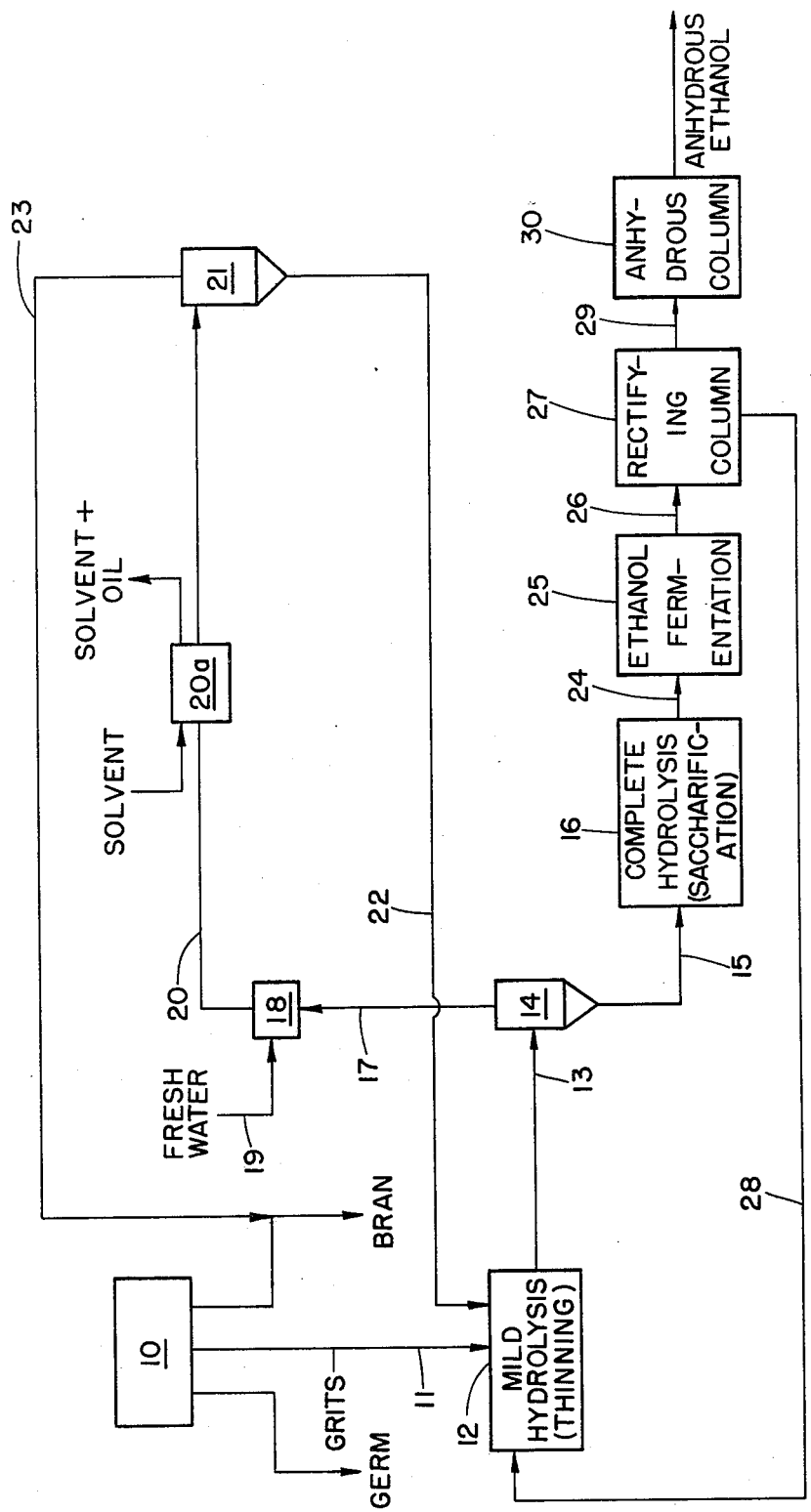

FERMENTABLE SUGAR FROM THE HYDROLYSIS OF STARCH DERIVED FROM DRY MILLED CORN

BACKGROUND OF THE INVENTION

1. Field of the Invention

This invention relates to the acid and/or enzymatic hydrolysis of starch derived from dry milled corn to provide fermentable sugar.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquifaction and saccharification), the fermentation of sugar to a dilute solution of ethanol ("beer") and the recovery of anhydrous ethanol by distillation, have been modified in numerous ways to achieve improvements in product yield, production rates and so forth (see, for example, U.S. Pat. No. 3,236,740 and the booklet "Industrial Alcohol by Continuous Fermentation and Vacuum Distillation With Low Energy Consumption", of Chemapec, Inc., Woodbury, New York). For ethanol to realize its vast potential as a partial or total substitute for petroleum fuels or as a substitute chemical feedstock, it is necessary that the manufacturing process be as efficient in the use of energy and raw materials as possible so as to maximize the energy return for the amount of ethanol produced and enhance the standing of the ethanol as an economically viable replacement for petroleum based raw materials. To date, however, relatively little concern has been given to the energy and raw material requirements for manufacturing ethanol from biomass and consequently, little effort has been made to minimize the thermal expenditure and waste incurred in carrying out any of the aforesaid discrete operations involved in the manufacture of ethanol from vegetative sources.

Processes for the enzymatic hydrolysis of starch to provide fermentable sugars are well known (viz., U.S. Pat. Nos. 2,219,668; 2,289,808; 2,356,218; 2,431,004; 2,676,905; 3,308,037; 3,337,414; 3,423,239; 3,425,909; 3,551,293; 3,565,764; 3,591,454; 3,592,734; 3,654,081; 3,720,583; 3,910,820; 3,912,590; 3,922,196; 3,922,197; 3,922,198; 3,922,199; 3,922,200; 3,922,201; 3,969,538; 3,988,204; 3,922,261; 3,966,107; 3,998,696; 4,014,743; 4,016,038; 4,017,363; 4,028,186; 4,032,403; and, C. Bos et al., "Experience with the DDS-Krøyer Direct Hydrolysis Process", Die Starke, Vol. 26, No. 6, 1974, pp. 181-184). Similarly, processes for the acid hydrolysis of starch to provide fermentable sugars are also well known (viz, U.S. Pat. Nos. 2,203,325; 2,210,659; 2,359,763; 2,393,095; 2,395,907; 2,565,404; 2,946,706; 2,954,304; 2,989,425; 3,169,083; 3,200,012; 3,236,687; 3,313,654; 3,446,664; 3,484,287; 3,607,395; and, 4,137,094). While these and similar processes are for the most part readily adaptable to the hydrolysis of the finely divided, relatively pure starch derived from conventional processes of wet milling corn, their application to the starch-containing fractions obtained from processes of dry milling corn as currently practiced would be uneconomically wasteful of the substantial amounts of protein and edible oil associated with these fractions. Wet milling processes typically remove all but an insignificant amount of nonstarch materials, i.e., protein, cellulosic fiber and oil, from the starch component of the corn kernel, the non-starch materials finding valuable application in their own right as animal feeds and feed supplements. However, from the standpoint of producing starch for conversion to sugar, the sugar to dilute ethanol and the dilute ethanol to essentially anhydrous ethanol, conventional wet-milling processes are undesirable because of the need to ultimately remove the large amounts of process water involved.

Where, as in the case of low cost industrial ethanol, a minimal use of energy is necessary to achieve an economically viable process, a relatively energy and capital intensive process such as one based on wet-milled corn starch as the starting material can be disadvantageous. For this reason, the hydrolytic conversion of starch derived from any of the known and conventional dry corn milling processes is especially desirable in an industrial scale anhydrous ethanol program since these processes employ no added water beyond the moisture which is already naturally present in the corn kernels. In a typical dry corn milling process, the kernels are broken by impact and the resulting fractions made up of grits and fine feed which contain the bulk of the starch and significant quantities of oil, protein and cellulosic fiber, germ which contains most of the oil content of the kernels, and hulls which contain the major portion of the fiber, are separated employing degerminators, sifters, aspirators and gravity separators. A typical dry corn milling product analysis (pounds per bushel) is as follows:

| DRY DEGERMINATION PRODUCTS ANALYSIS ON YELLOW CORN #2, LB/100LB (DRY BASIS) | | | | |
|---|---|---|---|---|
| | CORN | GERM | BRAN | GRITS |
| Yield, % | 100 | 10 | 8 | 82 |
| Ash | 1.63 | 0.45 | 0.32 | 0.86 |
| Fat (oil) | 4.30 | 2.20 | 0.36 | 1.74 |
| Protein | 9.00 | 1.36 | 0.56 | 7.08 |
| Fiber | 2.56 | 0.43 | 1.20 | 0.93 |
| Starch | 72.00 | 2.80 | 2.40 | 66.80 |
| Other $N^2$ Free Extract | 10.51 | 2.76 | 3.16 | 4.59 |
| Total | 100.00 | 10.00 | 8.00 | 82.00 |

As this analysis indicates, the grits contain 92.8% of the starch, 78.7% of the protein and 40.5% of the oil of the whole corn kernels. Direct complete hydrolysis of the grits would therefore make these substantial amounts of protein and oil unavailable for use as comestibles.

Accordingly, there has heretofore existed a need for a process for converting starch derived from dry milled corn to fermentable sugars while recovering substantially all of the protein and oil content of the starch component of the dry milled corn prior to the complete hydrolysis of the starch.

SUMMARY OF THE INVENTION

In accordance with the present invention, a process is povided for converting starch derived from dry milled whole corn, which starch contains relatively substantial amounts of water insoluble protein and oil and relatively small amounts of one or more water soluble components selected from the group consisting of sugar, lipid, protein, vitamin and mineral, to fermentable sugar to provid substrate for the thermally efficient largescale production of ethanol. An aqueous slurry of the starch is subjected to a mild, i.e., thinning or liquifying, hydrolysis to provide a sterile partial starch hydrolysate containing the water insoluble protein and oil and the water soluble components of the starch in a substantially unaltered condition. The slurry is then separated into an aqueous partial starch hydrolysate portion containing a part of the water soluble components and a water insoluble protein and oil portion containing the remaining part of the water soluble components. The aqueous partial starch hydrolysate portion is subjected to further hydrolysis and the resulting aqueous solution of fermentable sugar together with part of the water soluble component of the original starch feed is conveyed to a fermentation unit where conversion of the sugar to ethanol and further hydrolysis of any remaining partial starch hydrolysate to fermentable sugar takes place.

The water insoluble protein and oil portion may be combined with water to dissolve the water soluble components associated therewith with the resulting aqueous slurry thereafter being separated into a protein and oil portion substantially free of any of the water soluble components of the original starch, and an aqueous portion containing water soluble components. The protein and oil may be used directly in animal feed or, if desired, they may be separately recovered for individual use. The aqueous portion containing water soluble components of the starch is advantageously recycled for use in mildly hydrolyzing another quantity of starch.

Employing the foregoing starch hydrolysis process, only minimal quantities of fresh water need be used to accomplish conversion of the starch to fermentable sugar thus reducing the amount of water which must be removed from product ethanol obtained from the fermentation of the sugar, and consequently, the amount of thermal energy which must be expended in the manufacture of the ethanol. Moreover, substantially all of the water insoluble protein contained in the original starch can be recovered for other commercially valuable uses, notably animal feed, and due to the water recycle feature which is made possible by the process herein, a good portion of the water soluble components of the starch are retained in the solution of product fermentable sugar and are therefore available for satisfying certain nutrient requirements of the yeast employed in the fermentation of the sugar to ethanol.

The process herein with appropriate modification is also applicable to the hydrolysis of starch contained in degerminated corn, i.e., corn from which a portion of the oil has been removed, dehulled corn, and degerminated and dehulled corn.

The term "fermentable sugar" as used herein is to be understood as referring to a single fermentable sugar such as glucose (dextrose), fructose, maltose, or sucrose but more commonly will be applicable to these and similar fermentable sugar oligomers in admixture.

BRIEF DESCRIPTION OF THE DRAWING

The accompanying drawing is a diagrammatic flow sheet illustrative of the starch hydrolysis process of the present invention. The process contemplates the use of known and conventional equipment which is readily available from several suppliers.

DESCRIPTION OF THE PREFERRED EMBODIMENTS

Referring to the drawing, the conventional dry milling of corn carried out in unit 10 results in three fractions, the germ which contains most of the oil content of the corn kernels, the grits (combined with the fine feed) which contains most of the starch but also substantial amounts of water insoluble protein and oil and significant quantities of water soluble components as indicated above, and the bran or hulls, which contains the bulk of the fiber (cellulose) of the corn. While the process of this invention can be carried out upon the whole dried milled corn, i.e., corn containing substantially all of the oil content of the product, in the embodiment shown, hydrolysis is carried out upon corn grits, i.e., corn containing only a portion of the oil content of whole corn kernels. The starch fraction of the degerminated dry milled corn is conveyed through 11 to a mild hydrolysis unit 12 where the starch molecules are initially depolymerized to form partial hydrolysates. This first hydrolysis, i.e., thinning or liquefying, can be effected in a known manner employing as the hydrolyzing agent, a strong acid such as hydrochloric acid, sulphuric acid, phosphoric acid, nitric acid, etc., or a liquefying enzyme such as alpha-amylase. The operating conditions for hydrolysis are well known and do not in themselves constitute a part of this invention. In general, an initial acid hydrolysis is carried out with a sufficient amount of strong acid to provide a pH of from about 1.0 to about 2.5, this mild hydrolysis of the starch being carried out at a temperature of from about 160° F. to about 350° F. and preferably at a temperature of from about 200° F. to about 250° F. These temperatures are conveniently obtained by injecting steam into the hydrolysis unit. Pressures on the order of from about 5 to about 250 psig, and advantageously, from about 5 to about 150 psig, can be used. Residence time of the starch slurry in mild hydrolysis unit 12 to effect partial hydrolysis and sterilization of the starch is not a critical consideration. In general, residence times of up to about 15 minutes, and preferably of up to about 5 minutes, provide good results. Similarly, in a mild enzyme hydrolysis procedure, considerable latitude may be taken with respect to the amounts of hydrolyzing agent employed. Thus, for example, the starch slurry can be combined with from about 0.3 to about 3.0 lb. per 1,000 lb. of dry starch, and preferably from about 0.5 to about 1.0 lb. per 1,000 lb. of dry starch, of liquefying enzyme such as alpha-amylase, advantageously at a pH of from about 3.0 to about 6.0, and preferably at a pH of from about 4.0 to about 5.0, to promote maximum enzyme activity. The enzyme-containing gelatinized starch slurry can then be heated to a temperature of from about 160° F. to about 250° F., and preferably to a temperature of from about 200° F. to about 230° F., and held to within this temperature for a period of time sufficient to provide a pumpable slurry of partially hydrolyzed starch. Typically, the mild hydrolysis herein, regardless of the nature of the hydrolyzing agent employed, is conducted for a period of time which will yield a slurry containing from about 12 to about 24 dextrose equivalent (D.E.), and preferably from about 16 to about 20 D.E. Under the foregoing conditions of acid or enzyme hydrolysis, the accompanying water insoluble protein and oil and the water soluble components of the starch will remain substantially unaffected. The partially hydrolyzed starch stream is then conveyed through line 13 to a first centrifuge, filter or other separating device 14 where an aqueous partially hydrolyzed starch stream containing a portion of solubles is recovered as underflow through line 15 to undergo further hydrolysis to fermentable sugar in starch hydrolysis unit 16 and the stream of protein and oil containing the remaining portion of solubles is recovered as overflow through line 17 to be washed with fresh water entering unit 18 through line 19. The washed aqueous stream of protein and oil is conveyed through line 20, advantageously to an oil separating unit 20a, wherein the oil is removed in a known or conventional manner such as settling or extracting with a solvent, e.g., n-hexane, and the de-oiled protein stream is then passed to a second centrifuge, filter or other separating device 21 with the aqueous solubles-containing underflow being transferred through line 22 to satisfy part or all of the process water requirements of mild hydrolysis unit 12 in a subsequent starch conversion sequence. The protein overflow, largely devoid of water soluble components, is recovered from centrifuge 21 through line 23 where it can be combined with the bran fraction of the dry milled corn to provide a nutritious animal feed or feed supplement. Alternatively, the total wash stream 20 can be directly separated in 21 with the oil being used as a nutrient for animal feed. The further hydrolysis of the aqueous stream of partial starch hydrolysates in starch hydrolysis unit 16 also can be carried out with acid or enzyme.

If acid is contemplated, it is advantageous to effect hydrolysis in accordance with the process disclosed in commonly assigned copending U.S. patent application Ser. No. 91,640, filed Nov. 5, 1979. In this process, an acidified partially hydrolyzed starch stream is combined with relatively high pressure steam to provide either a single phase or dual phase flow through a tubular reaction zone where rapid hydrolysis of the partial hydrolysate to a level of at least about 60 weight percent, and preferably at least about 80 weight percent, of the solids content to fermentable sugar takes place. To prevent any further reaction which might result in production of unfermentable sugar, reversion or degradation products, the hydrolysis is abruptly ended by suddenly relieving the pressure from the hydrolysis medium. In a single phase (liquid) flow operation, the partially hydrolyzed starch slurry at a pressure which is in excess of the saturation pressure of water at the temperature of the slurry passing through the tubular reaction zone, e.g., at from about 10 to about 1,000 psig and preferably, from about 600 to about 900 psig, is combined with an amount of steam sufficient to heat the slurry in this zone to a temperature of from about 285° F. to about 430° F. and preferably, from about 320° F. to about 390° F. In a dual phase (liquid and steam) flow operation, the acidified partial starch hydrolysate slurry is combined with an amount of steam sufficient to provide a temperature of from about 285° F. to about 420° F. or higher at saturation pressure. If enzyme is contemplated, it is advantageous to carry out further hydrolysis in accordance with the process disclosed in commonly assigned copending U.S. patent application Ser. No. 043,191, filed May 29, 1979. In this process, the partially hydrolyzed starch slurry is combined with a saccharifying enzyme such as amyloglucosidase, advantageously together with a saccharification catalyst such as a source of calcium ion, under conditions of pH and temperature which promote maximum enzyme activity, e.g., a pH of from about 4.0 to about 5.0 and preferably from about 4.3 to about 4.7, and a temperature of from about 140° F. to about 145° F. Saccharification can proceed until such time as about 60 to about 70 weight percent of the solids content is obtained as fermentable sugar (2 to about 10 hours) with further saccharification being carried out in the fermentation unit.

Following further hydrolysis of the partial starch hydrolysates to fermentable sugar in 16, the latter is conveyed through line 24 to fermentation unit 25 with the dilute aqueous ethanol ("beer") resulting therefrom being sent through line 26 for concentration to about 90 volume percent, or higher, ethanol in rectifying column 27. The aqueous still bottoms from the rectifying column contain some proteins and other nutrients and are preferably recycled through line 28 to mild hydrolysis unit 12 to satisfy part of the water requirements of the starch conversion process herein. Such recycle further tends to minimize the use of water in the overall production sequence from starch to anhydrous ethanol and has the added advantage of retaining nutrients in the system which can be utilized by yeast used in the fermentation of the sugar to ethanol. Alternatively, the still bottoms in line 28 can be subjected to a drying operation with the residue therefrom being employed as a animal feed or feed supplement. The concentrated ethanol is conveyed through line 29 to anhydrous column 30 wherein azeotropic distillation to provide substantially water-free ethanol is carried out.

What is claimed is:

1. A process for converting the starch fraction derived from whole dry milled corn to a sterile aqueous solution of fermentable sugar, said starch containing water insoluble protein and oil and one or more water soluble components selected from the group consisting of sugar, lipid, protein, vitamin and mineral, which comprises:
   (a) liquefying an aqueous slurry of the starch by hydrolysis to provide sterile aqueous partial starch hydrolysate slurry containing the water insoluble protein and oil and the water soluble components in substantially unaltered condition;
   (b) separating the slurry resulting from liquefying step (a) into an aqueous sterile slurry of partial starch hydrolysate containing a part of the water soluble components and an aqueous slurry of water insoluble protein and oil containing the remaining part of the water soluble components; and,
   (c) saccharifying the relatively thin aqueous slurry of partial starch hydrolysate to provide a sterile aqueous solution of fermentable sugar.

2. The process of claim 1 wherein the corn feed for liquefying step (a) is dehulled corn.

3. The process of claim 1 wherein the sterile aqueous solution of fermentable sugar is subjected to fermentation to provide dilute aqueous ethanol.

4. The process of claim 3 wherein the dilute aqueous ethanol is concentrated in a rectifying column with the aqueous bottoms from said rectifying column being recycled for use in a subsequent liquefying step (a).

5. The process of claim 4 wherein the concentrated ethanol is substantially dehydrated to provide anhydrous ethanol.

6. The process of claim 1 further comprising the steps of:
   (d) diluting the aqueous slurry of water insoluble protein and oil resulting from step (b) with water;
   (e) separating water from the water insoluble protein and oil resulting from step (d); and,
   (f) recycling the water recovered in step (e) for use in a subsequent liquefying step (a).

7. The process of claim 1 wherein liquefying step (a) is carried out with enzyme.

8. The process of claim 1 wherein saccharifying step (c) is carried out with enzyme.

9. The process of claim 1 wherein liquefying step (a) is carried out with acid.

10. The process of claim 1 wherein saccharifying step (c) is carried out with enzyme.

11. A process for converting the starch fraction derived from dry milled degerminated corn to a sterile aqueous solution of fermentable sugar, said starch containing water insoluble protein, a relatively minor amount of the oil of the whole corn, and one or more water soluble components selected from the group consisting of sugar, lipid, protein, vitamin and mineral, which comprises:
   (a) liquefying an aqueous slurry of the starch by hydrolysis to provide sterile aqueous partial starch hydrolysate slurry containing the water insoluble protein and the water soluble components in substantially unaltered condition;
   (b) separating the slurry resulting from liquefying step (a) into an aqueous sterile slurry of partial starch hydrolysate containing a part of the water soluble components and an aqueous slurry of water insoluble protein containing the remaining part of the water soluble components;
   (c) saccharifying the aqueous slurry of partial starch hydrolysate to provide a sterile aqueous solution of fermentable sugar;
   (d) diluting the aqueous slurry of water insoluble protein from step (b) with water;
   (e) separating water from the water insoluble protein resulting from step (d); and,
   (f) recycling the water recovered in step (e) for use in a subsequent liquefying step (a).

12. The process of claim 11 wherein the corn feed for liquefying step (a) is degerminated, dehulled corn.

13. The process of claim 11 wherein the relatively minor amount of oil in the water insoluble protein fraction is removed therefrom.

* * * * *